(12) United States Patent
Bayer

(10) Patent No.: US 10,456,427 B2
(45) Date of Patent: Oct. 29, 2019

(54) METHOD OF TREATING VIRAL DISEASES AND PROLIFERATIVE DISORDERS

(71) Applicant: Robert C. Bayer, Orono, ME (US)

(72) Inventor: Robert C. Bayer, Orono, ME (US)

(73) Assignee: Lobster Unlimited LLC, Orono, ME (US)

( * ) Notice: Subject to any disclaimer, the term of this patent is extended or adjusted under 35 U.S.C. 154(b) by 468 days.

(21) Appl. No.: 15/177,293

(22) Filed: Jun. 8, 2016

(65) Prior Publication Data
US 2016/0279172 A1    Sep. 29, 2016

Related U.S. Application Data

(63) Continuation-in-part of application No. 14/948,338, filed on Nov. 22, 2015, now abandoned.

(60) Provisional application No. 62/172,402, filed on Jun. 8, 2015, provisional application No. 62/083,228, filed on Nov. 22, 2014.

(51) Int. Cl.
| | | |
|---|---|---|
| *A61K 35/612* | (2015.01) | |
| *A61K 38/17* | (2006.01) | |
| *A61K 9/08* | (2006.01) | |
| *A61K 35/644* | (2015.01) | |
| *A61K 39/00* | (2006.01) | |

(52) U.S. Cl.
CPC .............. *A61K 35/612* (2013.01); *A61K 9/08* (2013.01); *A61K 35/644* (2013.01); *A61K 38/1767* (2013.01); *A61K 39/0011* (2013.01); *A61K 2039/575* (2013.01); *A61K 2039/6031* (2013.01)

(58) Field of Classification Search
CPC ...... A61K 35/612; A61K 35/63; A61K 35/64; A61K 8/987; A61K 9/00; A61K 9/0014; A61K 35/644; A61K 38/1767; A61K 9/08; A61Q 19/00
See application file for complete search history.

(56) References Cited

U.S. PATENT DOCUMENTS

| | | |
|---|---|---|
| 5,231,081 A | 7/1993 | Stiefel et al. |
| 2009/0093738 A1 | 4/2009 | Merchant et al. |
| 2010/0255017 A1 | 10/2010 | Becker |
| 2011/0033499 A1 | 2/2011 | Cuthbertson |
| 2014/0234378 A1* | 8/2014 | Bayer .................... A61K 35/63 424/278.1 |
| 2016/0143958 A1* | 5/2016 | Bayer .................. A61K 35/612 424/538 |

OTHER PUBLICATIONS

HomeRemediesLook ("HRL" "Common Home Remedies to Get Rid of Warts" May 12, 2014, retrieved online <URL:http:// homeremedieslook.com/home-remedies-for-warts/>, 7 pages. (Year: 2014).*

Terwilliger, "Crustacean hemocyanin gene family and microarray studies of expression change during eco-physiological stress," Integrative and Comparative Biology, vol. 46, No. 6, pp. 991-999, Jul. 12, 2006; doi 10.1093/icb/ic1012.

Dolashka et al., "Antitumor Activity of Glycosylated Molluscan Hemocyanins via Guerin Ascites Tumor," 2011, pp. 130-149, Immunological Investigations.

Linn et al., "Keyhole Limpet Haemocyanin in Experimental Bladder Cancer," 2000, Abstract Only, ProQuest, Aquatic Sciences and Fisheries Abstracts.

The Lobster Conservancy, "Lobster Biology: Physiological Processes," retrieved from http://www.lobsters.org/tlcbio/biology5.html, 1 page. Date unknown, downloaded in 2004.

Olicard et al., "Putative antiviral activity in hemolymph from adult Pacific oysters, *Crassostrea gigas*," 2005, pp. 147-152, Science Direct, Antiviral Research, vol. 66.

Olicard et al., In vitro research of anti-HSV-1 activity in different extracts from Pacific oysters *Crassostrea gigas*, 2005, pp. 141-147, Diseases of Aquatic Organisms, vol. 67.

Pan et al., "A review on digestive enzymes in crustacean," 2002, Abstract Only, Journal of Ocean University of Qingdao/Qingdao Haiyang Daxue Xuebao.

Pan et al., "A review on digestive enzyme of crustacean larvae," 2006, Abstract Only, Journal of fishery sciences of China/Zhongguo Shuichan Kexue.

Liu et al., "Antiviral immunity in crustaceans," 2009, pp. 79-88, Fish & Shellfish Immunology, vol. 27.

Lee et al., "Early events in crustacean innate immunity," 2002, pp. 421-437, Fish & Shellfish Immunology, vol. 12.

Zhang et al., "Antiviral properties of hemocyanin isolated from shrimp *Penaeus monodon*," 2004, pp. 93-99, Science Direct, Antiviral Research vol. 61.

Greco et al., "Antiviral activity of the hemolymph of Lonomia obliqua (*Lepidoptera: Saturniidae*)," 2009, Abstract Only, PubMed, Antiviral Research, vol. 84.

Velkova et al., "Structure of hemocyanin from garden snail *Helix lucorum*," 2010, Abstract Only, PubMed, Comparative Biochemistry Physiology.

Zanjani et al., "Formulation of abalone hemocyanin with high antiviral activity and stability," 2014, Abstract Only, European Journal of Pharmaceutical Sciences, vol. 53.

PCT Search Report and Written Opinion issued in connection with corresponding International Application No. PCT/US16/36518 dated Sep. 16, 2016, 11 pages.

Jeffes III et al., "Actinic Keratosis, current treatment options," Am J Clin Dermatol. (2000) 1(3): 167-79.

Proksch, "The Skin: an indispensable barrier," Exp Dermatol. (2008) 17:1063-72.

Beale et al., "Anti-lipopolysaccharide factors in the american lobster homarus americanus: Molecular characterization and transciptional response to vibro fluvialis challenge." Comp Biochem Physiol Part D (2008) 3:263-9.

(Continued)

*Primary Examiner* — Aaron J Kosar
(74) *Attorney, Agent, or Firm* — Hoffman Warnick LLC

(57) ABSTRACT

Lobster hemolymph and compositions derived therefrom for the prevention or treatment of viral diseases or cancer by systemic administration.

30 Claims, 2 Drawing Sheets

(56) References Cited

OTHER PUBLICATIONS

Cancer Drug Information, Cancer Drug Information "FDA Approval of Imiquimod", <URL:www.cancer.gov/cancertopics/druginfo/fda-imiquimod>, retrieved Feb. 20, 2014.
NCI-NIH "Milestone (1971): National Cancer Act of 1971", http://dtp.nci.nih.gov/timeline/noflash/milestones/m4_nixon.htm, downloaded Feb. 20, 2014, archived online 2 pages.
Jemal et al., "Cancer Statistics, 2010," CA Cancer J Clin. (2010) 60:277-300.
Dictionary.com entry for lobster, downloaded Feb. 19, 2014, 4 pages.
Degrave et al., "A classification of living and fossil genera of decapod crustaceans," Raffles Bulletin of Zoology. (2009) Supl. No. 21:1-109.
Schoenback et al., "Observations on the effects of the folic acid antagonists, aminopetin and amethopterin, in patients with advanced neoplasms," Cancer. (1952) 5:1201-20.
Casares et al., "The american lobster, homarus americanus contains morphine that is coupled to nitric oxide release in its nervous and immune tissues: evidence for neurotransmitter and hormonal signaling," Neuroendocrin Let. (2005) 2 (26):89-97.
Restriction Requirement for U.S. Appl. No. 13/815,286, dated Sep. 20, 2013, 8 pages.
Non Final Office Action for U.S. Appl. No. 13/815,286, dated Mar. 17, 2014, 14 pages.
Non Final Office Action for U.S. Appl. No. 13/815,286, dated Oct. 3, 2014, 16 pages.
Final Office Action for U.S. Appl. No. 13/815,286, dated Jan. 29, 2015, 12 pages.
Notice of Allowance for U.S. Appl. No. 13/815,286, dated Apr. 13, 2015, 9 pages.

\* cited by examiner

METHOD OF TREATING VIRAL DISEASES AND PROLIFERATIVE DISORDERS

CROSS-REFERENCE TO RELATED APPLICATIONS

This application claims the benefit of U.S. Provisional Patent Application Ser. No. 62/172,402, filed 8 Jun. 2015 and is a continuation-in-part of co-pending U.S. patent application Ser. No. 14/948,338, filed 22 Nov. 2015, which claims priority to U.S. Provisional Patent Application Ser. No. 62/083,228, filed 22 Nov. 2014, the entire contents of each of which is incorporated herein as though fully set forth.

FIELD OF INVENTION

This invention is in the field of treatment of viral diseases and proliferative disorders by internally administering to a patient lobster hemolymph or compositions derived therefrom.

BACKGROUND

Lobster (*Homarus americanus*) hemolymph is a readily available byproduct of lobster processing that is currently discarded as waste.

There are approximately 215,000,000 pounds of lobster landed annually between the U.S. and Canada. We estimate that close to 60,000,000 pounds is processed by the food industry. The hemolymph from processed lobsters is currently discarded at an estimated rate of 2 million pounds per year.

*Homarus americanus* as a source of hemolymph is unique because lobster hemolymph/hemocyanin is readily available in sufficient volume to support its widespread use. This is not the case with hemolymph from other crustaceans and mollusks. Unlike shrimp, oysters, clams and other shellfish, lobsters contain a much larger volume of hemolymph—approximately 100 times more by volume. Additionally, unlike other shellfish, extraction of lobster hemolymph can be carried out during typical lobster processing. Though it is currently discarded, it can be harvested and utilized in our invention.

SUMMARY OF INVENTION

Our invention is a new utilization and a value-added product for the lobster industry. The invention provides for a formulation and process to utilize hemolymph, or its component hemocyanin, from the lobster (*Homarus americanus*, *Homarus gammarus*, and *Panulirus argus*) for the prevention or treatment of viral infections and proliferative disorders such as cancers.

In an illustrative embodiment, the method of the invention comprises internally administering to a mammal suffering from a viral infection or a proliferative disorder a pharmaceutical composition that is made from lobster hemolymph or its extracted hemocyanin (either in a natural state or a derivatized state) in combination with a pharmaceutically acceptable excipient, or as an adjuvant to an antiviral therapy or anti-cancer therapy.

In illustrative embodiments, the anti-viral and anti-cancer properties of lobster hemocyanin are enhanced by fractionation and/or glycosylation.

In illustrative embodiments, the inventions comprises a pharmaceutical composition formulated for internal administration comprising as an active pharmaceutical ingredient (i) lobster hemolymph or lobster hemocyanins, (ii) an active fraction of lobster hemocyanins, or (iii) a derivatized form of lobster hemocyanins or active fractions of such derivatized forms.

In illustrative embodiments, lobster hemolymph, lobster hemocyanin, or a derivative of lobster hemocyanin is employed as an adjuvant, i.e., an agent that stimulates the immune system of a mammal or is employed as an antiviral, i.e., an agent that has viracidal activity, or as both an immune system stimulator and a viracide.

In illustrative embodiments, lobster hemolymph, lobster hemocyanin, or a derivative of lobster hemocyanin is employed as an adjuvant, i.e., an agent that stimulates the immune system of a mammal or is employed as an anti-cancer agent, i.e., an agent that has tumoricidal activity, or as both an immune system stimulator and an anti-cancer agent.

BRIEF DESCRIPTION OF FIGURES

These and other features of the invention will be more readily understood from the following detailed description of the various aspects of the invention taken in conjunction with the accompanying drawings that depict various embodiments or aspects of the invention, in which.

Figure 1:
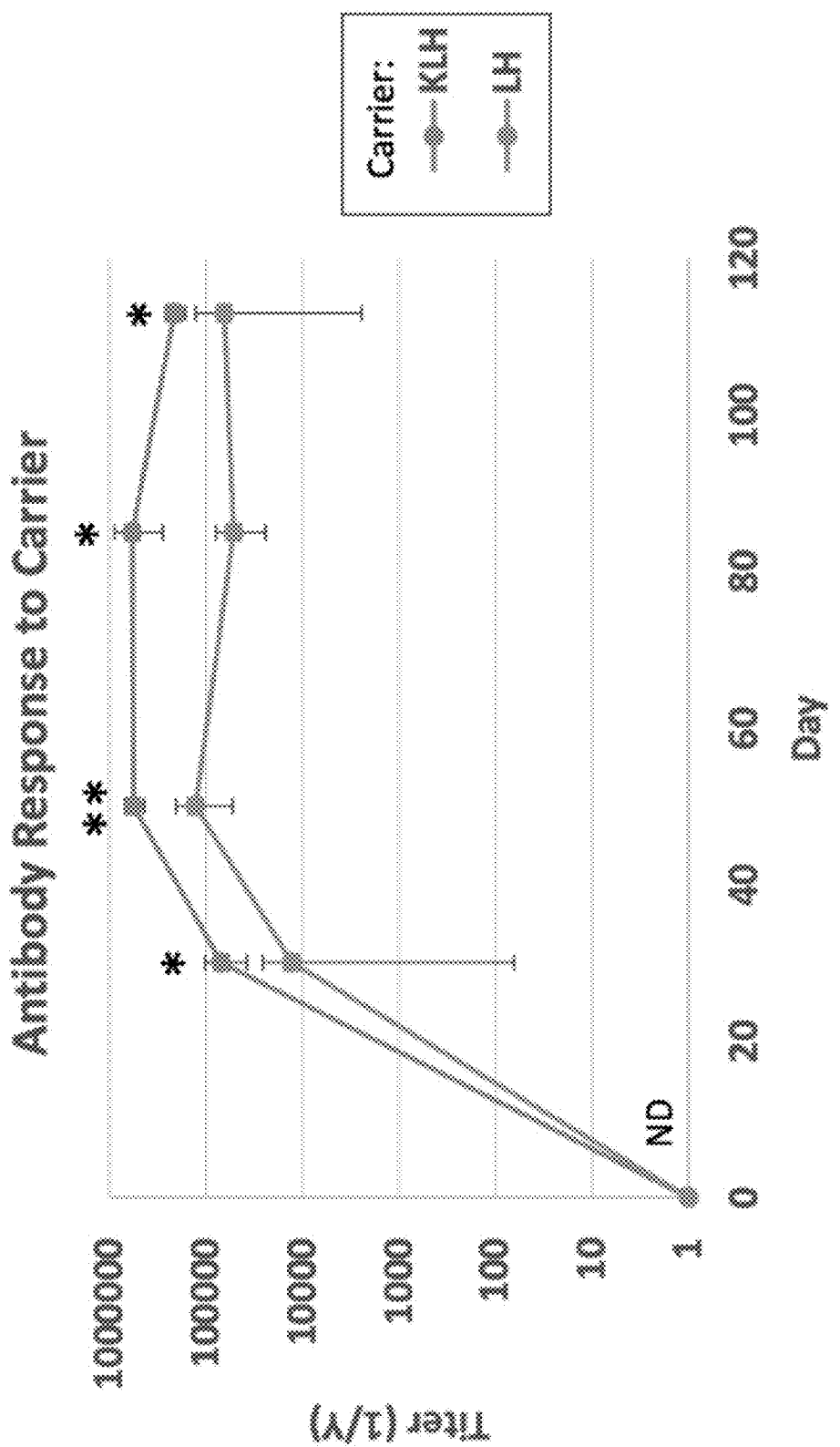
FIG. 1 is a graph showing that Keyhole Limpet Hemocyanion (KLH) elicits higher titer anti-carrier antibody responses than Lobster Hemocyanin (LH).

The drawings are intended to depict only typical aspects of the invention and therefore should not be considered as limiting the scope of the invention.

DETAILED DESCRIPTION OF INVENTION

This invention utilizes lobster hemolymph/hemocyanin as an anti-viral treatment of diseases like ebola, herpes, polio, HIV, Influenza (e.g., H1N1), measles, and others or as an anti-cancer agent. The term "proliferative disorder" encompasses all forms of disorders that are generally regarded and treated as cancers including without limitation solid tumors, non-solid tumors, dysplasias, and other cancers.

The hemolymph can be used as extracted from lobster or it can be diluted with a liquid carrier. Alternatively, the hemocyanin can be obtained in purified or partially purified form from lobster hemolymph by standard purification techniques including, e.g., centrifugation and chromatography. See, e.g., Bolton et al. ("Analytical and Semipreparative HPLC Analysis and Isolation of Hemocyanin from the American Lobster *Homarus americanus*," J Shellfish Res. 33(1):11-17 (2014)).

Derivatives of lobster hemolymph useful in the practice of this invention include, e.g., fragmented lobster hemocyanin, an active fraction of lobster hemocyanin or of fragmented hemocyanin, or a glycosylated form of lobster hemocyanin or of fragmented lobster hemocyanin.

Fragmentation by proteolytic enzymes along with glycosylation also allows for recombination into larger molecules that are more active and stable. Lobster hemocyanin has increased activity following fragmentation with proteolytic enzymes or sonication. Fragmented hemocyanin can be prepared by admixing and reacting a protease with lobster hemocyanin for a time and under conditions such that the hemocyanin is proteolyzed. Proteolytic enzymes include but are not limited to subtilisins. Thus, derivatives of lobster hemolymph useful in the practice of the invention can also be prepared by fragmenting the hemocyanin.

Active fractions of lobster hemocyanin are fractions of the hemocyanin or of fragmented hemocyanin that stimulate the immune system and induce or enhance the immune response to a virus with which the mammal is infected or may become infected and/or have direct antiviral activity. Derivatives of lobster hemolymph comprising such active fractions can be prepared such as by separating the component hexamers and dodecamers, e.g., as described by Bolton et al. (2014).

Hemocyanin-enriched fractions of hemolymph can be prepared, e.g., by low speed centrifugation of whole hemolymph to remove cells and collecting the supernatant. Hemocyanins can be further purified such as by high speed centrifugation, ion exchange chromatography, and/or dialysis. In an illustrative embodiment, a hemocyanin enriched fraction is prepared by allowing the hemolymph to stand whereby a precipitate is formed and the supernatant can be decanted and then subjected to further purification, e.g., by micofiltration.

Hemocyanin compositions useful in the present invention can be prepared, e.g., as disclosed by Stiefel et al., U.S. Pat. No. 5,231,081.

Adding sugars, including but not limited to sucrose, fructose, and trehalose to lobster hemocyanin enhances stability and can also enhance the immune stimulating and/or antiviral and/or anti-cancer activity of the hemocyanin. See, e.g., Zanjani, et al. ("Formulation of abalone hemocyanin with high antiviral activity and stability," European Journal of Pharmaceutical Sciences, 53:77-85 (2014)). A similar effect can be obtained by mixing the hemocyanin or a derivative thereof with honey, e.g., from *Apis mellifera*. The hemocyanin that has been mixed with or otherwise treated with one or more sugars, including by admixing with honey, are herein referred to as "glycosylated forms" of lobster hemocyanin or of derivatives thereof.

Data demonstrate that glycosylated lobster hemocyanin is more effective at reducing viral load in HSV-infected cells than non-glycosylated lobster hemocyanin. The increase in potency resulting from mixing honey with the hemolymph, or the hemocyanin fraction, may be the result of one or more, possibly all, of the sugars becoming covalently linked to the hemocyanin to form glycohemocyanin. Alternatively, it may be the case that mixing the hemocyanin with the honey is sufficient to enhance potency without formation of glycohemocyanin. In any event, the hemocyanin mixed with honey is herein referred to as glycosylated (irrespective or whether or not the some or all of the sugars are covalently bound to the hemocyanins).

In an illustrative glycosylation procedure, honey is added to a liquid carrier to a concentration of about 0.5% to about 5% (e.g., 1% in minimal essential media), followed by filter sterilization. Then isolated hemocyanin (isolated, e.g., by centrifugation of hemolymph followed by suspension in PBS at a concentration of 0.5 to 2 g/mL) is added to the liquid carrier to a final concentration of about 1% to about 50% (e.g., 10% hemocyanins in a 1% honey solution/mixture), followed by filter sterilization. The composition can be diluted prior to administration (e.g., 1:2 to 1:20, e.g., 1:10).

In an illustrative procedure, honey is added to a liquid carrier to a concentration of about 0.5% to about 5%, e.g., 1% in minimal essential media. Then isolated hemocyanin (isolated, e.g., by centrifugation of hemolymph) is added to the liquid carrier to a final concentration of about 1% to about 50%, e.g., 10% hemocyanins in a 1% honey solution/mixture.

Natural honey comprises >80% carbohydrates, the most abundant ones being fructose and glucose with less abundant ones including the disaccharides maltose, sucrose, isomaltose, maltulose, turanose and kojibiose and complex sugars. The invention comprises use of natural honey, with all of its naturally occurring carbohydrates, as well as use of a defined composition of one or more of such sugars, e.g., an aqueous solution comprising 50% to 90% total sugars, such as but not limited to 10% to 90% fructose+10% to 90% glucose.

Additional experiments demonstrated that lobster hemocyanin can be effective in treating cancerous cells, specifically, adenocarcinoma cells.

A mammal treated in accordance with this invention can be, e.g., a farm animal such as a pig, sheep, horse, or cow, a companion animal such as a dog, cat, rabbit, or ferret, or a primate such as a monkey, ape, or human being.

Derivatives of lobster hemocyanin suitable for use as adjuvants or for the prophylaxis or treatment in accordance with embodiments of the invention may be selected from the group consisting of a hexamers, dodecamers, and polypeptide subunits of the hemocyanin, active fragments of such multimers and polypeptides, and synthetically glycosylated forms of the polypeptides present in the hemocyanin, active fractions, or active fragments. Suitable hemocyanin derivatives for use in an embodiment of the invention can be identified such as by antiviral assays based on cell viability. For example, a cell line infected with the virus of interest or which is exposed to the virus can be treated with hemocyanin or a derivative thereof, and the efficacy of the treatment evaluated. Derivatives of hemocyanin used in methods and compositions embodied by the invention will typically have substantially the same antiviral activity as the intact hemocyanin or the antiviral activity will be enhanced generally or with respect to a particular virus or group of related viruses.

The lobster hemolymph or lobster hemocyanins, active fraction of lobster hemocyanins, or derivatized form of lobster hemocyanins or active fractions of such derivatized forms may be administered for prophylaxis or treatment of infection, physical manifestations and/or symptoms by a virus selected from, but not limited to, the group consisting of ebola viruses, Herpes viruses and in particular Herpes Simplex viruses (e.g., HSV-1 (predominantly oral) and HSV-2 (predominantly genital)), Herpes Zoster (VZV), Equine Herpesvirus-1 (EHV-1), Feline Herpesvirus-1 (FHV-1), Epstein-Barr virus (EBV), Human Immune Deficiency virus (HIV), Cytomegalovirus (CMV), human papilloma virus (HPV), rhinovirus, influenza virus (e.g., H1N1), and common cold viruses.

The lobster hemolymph or lobster hemocyanins, active fraction of lobster hemocyanins, or derivatized form of lobster hemocyanins or active fractions of such derivatized forms may be administered for prophylaxis or treatment of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia is also contemplated by this invention. Indications may include, but are not limited to brain cancers, skin cancers, bladder cancers, ovarian cancers, breast cancers, gastric cancers, pancreatic cancers, colon cancers, blood cancers, lung cancers and bone cancers. Examples of such cancer types include neuroblastoma, intestine carcinoma such as rectum carcinoma, colon carcinoma, familiarly adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

When used as an adjuvant, the hemocyanin or derivative thereof can be co-administered with the antigen(s) against which the immune response is to be directed. Such co-administration can comprise administration of a single pharmaceutical composition comprising both the hemocyanin or derivative thereof and the antigen(s) or in multiple compositions, simultaneously or sequentially. Co-administration can also be accomplished by coupling of the hemocyanin or derivative to the antigen(s). Thus, in an illustrative embodiment of the invention, lobster hemocyanin is conjugated to an antigen in much the same manner as giant keyhole limpet hemocyanin (KLH) is presently used for commercial and research purposes.

It has been found, however, that lobster hemocyanin is about as effective as KLH in stimulating an immune response to a conjugated antigen but is less antigenic than KLH. Specifically, data provided below demonstrate that lobster hemocyanin ("LH") stimulates equivalent antibody titer with respect to the antigen of interest but a lower antibody titer with respect to the carrier.

The antigen(s) can be any molecule to which an immune response can be generated. The antigen can, for example, be a viral, bacterial or other microbial antigen, or a mammalian cell antigen. The antigen may be, for example, a viral antigen such as an outer membrane protein or other suitable antigen or a mammalian cancer antigen, i.e., a tumor-specific antigen or a tumor-associated antigen. The antigen can be a whole molecule or a fragment thereof containing an epitope presented by the intact pathogen or mammalian cancer cell. The antigen may also be a hapten, which by itself is non-immunogenic or poorly immunogenic.

The lobster hemocyanin or derivative thereof, which can be administered systemically, i.e., non-topically, with or without an adjuvant and with or without an antigen, is administered internally. In illustrative embodiments, the lobster hemocyanin or derivative thereof, with or without an adjuvant or an antigen, is delivered systemically. Suitable routes of administration include, e.g., oral, transdermal, transmucosal (e.g., sublingual), and parenteral (e.g., subcutaneous, intramuscular, intravenous, and intrathecal).

It will be understood that the amount of the composition actually administered will be determined by a physician, in the light of the relevant circumstances including the condition to be treated, the choice of composition to be administered, the chosen route of administration, the age, weight, and response of the individual patient, and the severity of the patient's symptoms.

For therapeutic or prophylactic use, lobster hemolymph or lobster hemocyanin or a derivative thereof as described hereinabove will normally be administered as a pharmaceutical composition comprising as the (or an) essential active ingredient the lobster hemolymph or lobster hemocyanin or a derivative thereof in association with a solid or liquid pharmaceutically acceptable carrier and, optionally, with pharmaceutically acceptable adjuvants and excipients employing standard and conventional techniques.

The phrase "pharmaceutical composition" refers to a composition suitable for administration in medical (or veterinary) use. It should be appreciated that the determinations of proper dosage forms, dosage amounts, and routes of administration for a particular patient are within the level of ordinary skill in the pharmaceutical and medical or veterinary arts. The pharmaceutical compositions include suitable dosage forms for oral, parenteral (including subcutaneous, intramuscular, intradermal, intravenous, transdermal (such as via a dermal patch, gel, microneedle, iontophoresis, sonophoresis, or phonophoresis), bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product, e.g., a lyophilisate, for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and the like may be utilized. Injectable suspensions also may be used, in which case conventional suspending agents may be employed. Conventional preservatives, buffering agents and the like also may be added to the parenteral dosage forms. See, for example, Remington's Pharmaceutical Sciences, Mack Publishing Company, Easton, Pa., 17th edition, 1985. For parenteral administration, the hemolymph, hemocyanin, or a derivative of hemocyanin would be sterilized, e.g., by filtration of a hemocyanin-enriched fraction of hemolymph or cell-free hemocyanin or hemocyanin derivative.

In making pharmaceutical compositions containing lobster hemolymph or lobster hemocyanin or a derivative thereof as described hereinabove, the active ingredient(s) will usually be mixed with a pharmaceutically acceptable carrier, or diluted by a carrier, or enclosed within a carrier, which may be in the form of a capsule, sachet, paper, or other container. When the carrier serves as a diluent, it may be a solid, semi-solid, or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

The term "pharmaceutically acceptable" refers to compositions, carriers, diluents and reagents, that can be administered to a mammal, e.g., to a human being. Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxy-benzoates, talc, magnesium stearate, honey, and mineral oil. The formulations can additionally include lubricating agents, wetting agents, emulsifying and suspending agents, preserving agents, sweetening agents, or flavoring agents. The compositions of the invention may be formulated so as to provide quick, sustained or delayed release of the active ingredient after administration to the patient.

Compositions suitable for parenteral administration conveniently comprise a sterile aqueous preparation of a compound or composition of the invention, which is preferably isotonic with the blood of the recipient. This aqueous preparation may be formulated according to known methods using suitable dispersing or wetting agents, emulsifying and suspending agents. Various antibacterial and antifungal agents, for example, parabens, chlorobutanol, phenol, and sorbic acid also may be included. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Prolonged absorption of the injectable pharmaceutical form can be brought about by the use of agents delaying absorption, for example, aluminum monostearate and gelatin. Carrier formulation suitable for subcutaneous, intravenous, intramuscular, etc. administrations can be found in Remington's Pharmaceutical Sciences, Mack Publishing Co., Easton, Pa.

The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with the required pharmaceutical carrier. So, e.g., a pharmaceutical composition in intravenous unit dose form may comprise a vial or pre-filled syringe, each comprising an effective amount or a convenient fraction of an effective amount such that one the contents of one vial or syringe are administered at a time.

The present invention relates to a liquid, ointment, tablet, powder and/or crystals made from lobster hemolymph or its component hemocyanin (in its natural form and/or fractionated and glycosylated) for the treatment of viral infections and resulting lesions. The hemolymph is rendered particularly but not exclusively from the lobster genus: species *Homarus americanus*. Fractionation by proteolytic enzymes offers the possibility of recombination into larger molecules that are more active.

The invention also finds particular but not exclusive application for the treatment of viral diseases including but not limited to poliomyelitis (polio), HIV, Influenza (e.g., H1N1), and rubeola (measles).

Particularly in the case of treatment of a proliferative disorder, the present invention can be carried out in conjunction with other treatment approaches, e.g., in combination with a second or multiple other active pharmaceutical agents, e.g., biologic or chemotherapeutic agents, or with chemoradiation. Such other active pharmaceutical agents can include, without limitation, the chemotherapeutic agents described in "Modern Pharmacology with Clinical Applications", Sixth Edition, Craig & Stitzel, Ch. 56, pp 639-656 (2004), herein incorporated by reference in its entirety. Such additional agent can be, but is not limited to, Interferon-alpha, Interferon-beta, Interferon-lamda, alkylating agents, antimetabolites, anti-tumor antibiotics, plant-derived products such as taxanes, enzymes, hormonal agents, miscellaneous agents such as cisplatin, monoclonal antibodies, glucocorticoids, mitotic inhibitors, topoisomerase I inhibitors, topoisomerase II inhibitors, immunomodulating agents such as interferons, cellular growth factors, cytokines, and non-steroidal anti-inflammatory compounds (NSAID), cellular growth factors and kinase inhibitors. Other suitable classifications for chemotherapeutic agents include mitotic inhibitors, and anti-estrogenic agents.

Specific examples of suitable biological and chemotherapeutic agents include, but are not limited to, carboplatin, cisplatin, carmustine (BCNU), 5-fluorouracil (5-FU), cytarabine (Ara-C), 5-azacytidine (5-AZA), gemcitabine, methotrexate, daunorubicin, doxorubicin, dexamethasone, irinotecan, topotecan, etoposide, paclitaxel, docetaxel, vincristine, tamoxifen, TNF-alpha, TRAIL and other members, i.e., other than TRAIL and TNF-alpha, of the TNF superfamily (TNFSF) of molecules including agonists of TNFSF receptors like agonistic DR4- and DR5-directed antibodies, Interferon-alpha, Interferon-beta, thalidomide, thalidomide derivatives such as lenalidomide, melphalan, and PARP inhibitors. Other specific examples of suitable chemotherapeutic agents include nitrogen mustards such as cyclophosphamide, alkyl sulfonates, nitrosoureas, ethylenimines, triazenes, folate antagonists, purine analogs, pyrimidine analogs, anthracyclines, bleomycins, mitomycins, dactinomycins, plicamycin, *vinca* alkaloids, epipodophyllotoxins, taxanes, glucocorticoids, L-asparaginase, estrogens, androgens, progestins, luteinizing hormones, octreotide actetate, hydroxyurea, procarbazine, mitotane, hexamethylmelamine, carboplatin, mitoxantrone, monoclonal antibodies, levamisole, interferons, interleukins, filgrastim and sargramostim.

Useful chemotherapeutic agents include, but are not limited to, alkylating agents (e.g., cyclophosphamide, mechlorethamine, chlorambucil, melphalan), anthracyclines (e.g., daunorubicin, doxorubicin, epirubicin, idarubicin, mitoxantrone, valrubicin), cytoskeletal disruptors (e.g., paclitaxel, docetaxel), epothilones (e.g., epothilone A, epothilone B, epothilone D), inhibitors of topoisomerase I and II (e.g., irinotecan, topotecan, etoposide, teniposide, tafluposide), nucleotide analogs precursor analogs (e.g., azacitidine, azathioprine, capecitabine, cytarabine, doxifluridine, fluorouracil, gemcitabine, mercaptopurine, methotrexate, tioguanine), peptide antibiotics (e.g., bleomycin), platinum-based agents (e.g., carboplatin, cisplatin, oxaliplatin), retinoids (e.g., all-trans retinoic acid), and *vinca* alkaloids and derivatives (e.g., vinblastine, vincristine, vindesine, vinorelbine). In some embodiments, chemotherapeutic agents include fludarabine, doxorubicin, paclitaxel, docetaxel, camptothecin, etoposide, topotecan, irinotecan, cisplatin, carboplatin, oxaliplatin, amsacrine, mitoxantrone, 5-fluoro-uracil, or gemcitabine.

Example 1

Materials and Methods

Collection of Hemolymph

Hemolymph was collected by syringe from a sample size of 22 lobsters. Hemolymph was collected on the ventral side of the lobster with 10 mL needles by inserting in between the shell plates and drawing the blood. A total of about 105 mL of hemolymph was collected for the lab experiments.

Hemocyanin Preparation

Hemolymph from collection was pooled into equal sized sample containers, allowed to clot, and frozen at −20 C, then held for three days. A process for hemocyanin preparation in Bolton et al. was followed. After 3 days, samples were thawed and the hemolymph was pooled. The hemolymph with clotted material was then homogenized using a glass tissue homogenizer and liquid poured off into a beaker. The pooled hemolymph was then divided into two 50 mL centrifuge tubes and spun 1600 g for 12 min, found to still have particulate matter, then spun again at 3022 g for 20 min. The resulting hemolymph supernatant was poured off for future use and the pellet discarded. The supernatant was divided into two equal volumes and one was frozen for retention, the other used for the ultracentrifugation process.

Hemocyanin Purification with Ultracentrifugation

Eight ultracentrifuge tubes individually weighed and labeled. Equal amounts of prepared hemolymph were pipetted into eight ultracentrifuge tubes. These were then centrifuged at 142000 g for 7 hours at 5 degrees Celsius. The supernatant was pipetted off and frozen for retention. The weight of the tube with the pellet was taken and recorded to calculate yield. Phosphate buffer saline (PBS) was added to each tube to dissolve the pellet (0.5 mL) and preserve the hemocyanin.

Cell Culture Preparation

All cell culture took place in a laminar flow hood to avoid contamination. Media for cell culture was prepared by adding 50 mL fetal bovine serum (FBS) and 500 uL gentamycin (gent) to 500 mL of minimum essential media (MEM) in the MEM media bottle.

293T POI cells, or human embryonic kidney cells (HEK) were used for the experiments. A 75 $cm^2$ flask was prepared by adding 15 mL of our MEM media with gent and FBS. The cells were quickly thawed and added to the flask with the media and then incubated at 34 C with 5% $CO_2$ until a monolayer was produced.

Passing Cells for Experiments

Once the cells formed a monolayer the cells were passed for maintaining the cell line. This was done by preparing 3-4 flasks by added 15 mL of the MEM media with gent and FBS. The media in the current flask was poured off, 10 mL of PBS was added to rinse the cells, then 5 mL of trypsin was added to detach cells from flask bottom. After the addition of trypsin the flask was immediately put under a microscope to view when cells were detached and ready for the next step. This was determined by seeing clumps of cells floating through the media when the flask was rocked back and forth under the microscope. The trypsin was poured off at this point. The flask cap was tightened and the flask tapped to detach cells from the flask bottom. Then 5 mL of MEM media with gent and FBS was added to the flask and washed over the flask bottom to collect cells. A pipette was then used to draw up the 5 mL and 1 mL was deposited in each flask with leftover cells being put in liquid waste. This created a 1:5 cell transfer and was repeatedly performed throughout the research every three days for cell culture maintenance.

Preparation of Virus

From the American Type Culture Collection (ATCC) we obtained Herpes simplex virus 1 strain F (VR-733 Lot 60286834). The frozen virus was thawed and inoculated onto one 75 $cm^2$ flasks with 1.2 mL of HSV1. The flask was prepared for this by pouring off most of the media and the virus added to the flask. The flask was then over a two hour period rocked back and forth to increase virus-cell attachment. This was done in the incubator at 34 C with 5% $CO_2$. After that 2 hour period 15 mL of MEM media with gent and FBS was added to the flask and the cells were placed back in the incubator. After 24 hours 100% cytopathogenic effect (CPE) was observed. The supernatant from the flask containing all the virus was collected and 1 mL aliquots were frozen for future use.

TCID50 Test of Virus

To determine CPE effect of the virus a tissue culture infectious dose 50 test (TCID50) was completed. This was done by first seeding a 96-well plate by using 1 mL of HEK cells from a cell passing. The cells were suspended in 10 mL of MEM media and then poured into a sterile well. 100 uL were added to each well using a multichannel pipet. The 96-well plate was allowed to incubate overnight for cell adherence.

The serial dilution for this test was prepared by adding 900 uL of MEM media with gent and no FBS into 10 wells of a 24 well plate. Then 100 ul of virus was added to the first well to create a 1:10 dilution. The serial dilution was performed by taking 100 ul from the previous well and adding it to the next.

The 96-well plate was taken from the incubator and labeled from −2 to −10 with three control wells at the far right of the plate. Starting from the lowest dilution of the virus, −10, 100 uL of the virus was added to each well to get 8 wells with each dilution. The three columns of control wells had 100 uL MEM with gent added to them.

Results were viewed 24 hours and 48 hours after inoculation of the virus. CPE was determined by death of cells, refractile rounding and cell clumping.

Preparation for Cytotoxicity Test

For this test four 96-well plates were prepared in the same manner as in the TCID 50 in seeding the plates and the plates were incubated for 24 hours before use.

The hemocyanin sample was thawed and divided into 2 parts with one part being refrozen for use during TCID50 with hemocyanin and virus. We prepared MEM with gent and added 1% honey by adding 1 mL into 9.9 mL and then filter sterilizing to prepare a media for hemocyanin. Then 1 mL of hemocyanin was added to 9 mL of the MEM with gent and honey. To prepare the non-glycosylated hemocyanin we added 1 mL of hemocyanin to 9 mLs of MEM with gent.

Both of these hemocyanin samples were filter sterilized. For the test, 1:5 dilutions were created with the hemocyanin in MEM media with gent and FBS and the same with the glycosylated hemocyanin. Rough concentrations of hemocyanin were determined using the yield from the ultracentrifugation and that about 90% of protein content in the hemolymph is hemocyanin. As a result our dilutions had concentrations of 47915 ug/mL, 9583 ug/mL, 1917 ug/mL, 384 ug/mL, 77 ug/mL.

Preparation of Plates for Cytotoxicity Test

Two plates were labeled for the normal hemocyanin at 24 hours and 48 hours and the same for the glycosylated hemocyanin. Each of the dilutions and the negative control were given two columns on the plate with the bottom row of the plate being the positive control. Each well received 100 uL of their respective dilution or media with the positive control receiving sodium dodecyl sulfate (SDS) solution. The plates were then incubated at 34 C with 5% $CO_2$ for their respective times.

Neutral Red Assay for Cytotoxicity

Once the plates were prepared the neutral red (NR) working solution and Leibovitz's L-15 with neutral red was prepared. The neutral red working solution was created by adding 60 mg of stain to 15 mL of PBS solution and filtered through a 0.2 um syringe filter, wrapped in foil, and refrigerated until needed.

The L-15 with NR was prepared by adding 400 uL of NR to 40 mL of MEM with gent and incubated overnight. We found that for the 24 hour plates we nearly ran out so we mixed 400 uL of NR to 50 mL of MEM with gent for the 48 hour plates. Each L-15 with NR was covered with tin foil and incubated for 24 hours prior to use at 34 C with 5% $CO_2$.

After 24 hours of incubation, the two plates labeled, for 24 hours had their media aspirated. To each well 200 uL of the prepared L-15 with NR was added using a multichannel pipet and incubated for 2.5 hours at 34 C with 5% $CO_2$.

The L-15 with NR was aspirated off after the incubation time and the cells were washed in a 0.5% formalin and 1% $CaCl_2$ solution using a multichannel pipet and adding 200 uL to each well. We let this sit for 1 minute and then aspirated the liquid off and inverted the plate to blot on a paper towel.

Next 200 uL was added to each well of 1% acetic acid and 50% EtOH. The two plates were incubated at room temperature for 10 minutes.

Results were read using a BioTek® microplate reader and the absorption data were recorded in an Excel® file.

At the 48-hour mark the same procedure for the 24 hour plates was applied to the last two plates.

The results of this determined that we could use any concentration we had of hemocyanin for our last experiment because there was little cytotoxic effect from the hemocyanin on the HEK cells.

TCID50 Test of Hemocyanin Samples

Five plates were prepared for the last test by methods previously stated in seeding the plates. Each plate was labeled as follows: control, 47915 ug/mL hemocyanin, 1917 ug/mL hemocyanin, 47915 ug/mL hemocyanin with glycosylation, and 1917 ug/mL hemocyanin with glycosylation.

These dilutions were prepared by thawing what was left of our hemocyanin. Two samples were created with one solution containing the pure hemocyanin and the other being glycosylated. We did this by adding 2 mL of our hemocyanin to 18 mL of MEM with gent and that being filter sterilized. Next we prepared the glycosylation sample by adding 2 mL of hemocyanin to 18 mL of MEM with gent and 1% honey. Next we prepared 1:10 dilutions of both of those solutions to get two glycosylated samples and two normal hemocyanin samples at the above concentrations.

HSV1 virus was prepared by thawing and adding 1 mL of virus to 9 mL of MEM with gent and FBS. A serial dilution was conducted to -8.

The five plates were prepared by aspirating off the media one at a time and using five sterile well boats adding 100 uL of the assigned media to each plate. The plates were each labeled from -1 to -8 with the last four columns to be reserved as a control. 100 uL of diluted virus was added to each assigned well working from lower concentration to highest. Lastly the control wells were given 100 uL of MEM with gent and FBS. Plates were then incubated at 34 C with 5% $CO_2$.

Results looking for CPE were recorded at about 24, 48, and 72 hours upon start of incubation.

Results

Hemocyanin Purification with Ultracentrifugation

After ultracentrifugation we poured off the supernatant and weighed the pellet, which was our yield. Since about 90% of lobster hemolymph protein is hemocyanin we calculated how much hemocyanin we had in our pellet and so what we had for a concentration in the PBS solution. We had an end concentration of 0.9583 g hemocyanin/mL.

Control TCID50 Test of Virus

The results of the ATCC HSV1 virus plate reading showed that CPE occurred to the -4 to -5 dilution range. We found the viral titer to be $1*10^6.3$ TCID50/mL.

Neutral Red Assay for Cytotoxicity

The readings for the plates showed that there was minimal cytotoxicity but it did not result in complete cytotoxicity as in our SDS control. This meant that we could use the higher concentration of hemocyanin without causing harm to the cells.

TCID50 Test of Hemocyanin Samples

We determined the titer from the visual results of the experiment and determined that a drop in titer of 2-log difference shows good antiviral effect.

We found the control plate viral titer, which represented the collected virus from collection earlier in the experiment to be $1*10^4.7$ TCID50/mL and the highest concentration of hemocyanin at 47915 ug/mL to be $1*10^2.8$ TCID50/mL and glycosylated hemocyanin at 47915 ug/mL to be $1*10^2.5$ TCID50/mL. The titers for the lower concentrations, both 1917 ug/mL, hemocyanin and glycosylated hemocyanin were $1*10^4.0$ TCID50/mL.

Discussion

From the different experiments we were able to determine concentrations of hemocyanin that did not exhibit cytotoxicity of HEK cells.

From the TCID50 test it was visually seen in the -1 columns of the highest concentration that the virus' CPE effect on the cells was greatly limited. Whereas in the lower concentrations or in the control the first column showed complete cell death. The higher concentrations did not, but rather more cells lived. There was also delayed viral CPE effect in the hemocyanin and glycosylation samples. In regards to the viral titer the -2 log decrease in viral titer is close to being seen. Statistical analysis would put the results in the range of hemocyanin showing good antiviral activity against HSV1.

TABLE 1

| Sample | Log Virus dil | Infected | Cumulative infected | Cumulative uninfected | Ratio A/(A + B) | % infected | Proportionate distance | Log TCID50 |
|---|---|---|---|---|---|---|---|---|
| HSV HEK | -4 | 8/8 | 14 | 0 | 1.00 | 100.0 | | |
| MRH | -5 | 5/8 | 6 | 3 | 0.67 | 66.7 | 0.3 | 6.3 |
| Control | -6 | 1/8 | 1 | 10 | 0.09 | 9.1 | | |
| | -7 | 0/8 | 0 | 18 | 0.00 | 0.0 | | |

TABLE 1-continued

| Sample | Log Virus dil | Infected | Cumulative infected | Cumulative uninfected | Ratio A/(A + B) | % infected | Proportionate distance | Log TCID50 |
|---|---|---|---|---|---|---|---|---|
| HSV HEK | −3 | 8/8 | 10 | 0 | 1.00 | 100.0 | 0.7 | 4.7 |
| MRH | −4 | 2/8 | 2 | 6 | 0.25 | 25.0 | | |
| Exp Control | −5 | 0/8 | 0 | 14 | 0.00 | 0.0 | | |
| HSV HEK | −1 | 8/8 | 8 | 0 | 1.00 | 100.0 | 0.5 | 2.5 |
| MRH | −2 | 0/8 | 0 | 8 | 0.00 | 0.0 | | |
| 50K GLY | −3 | 0/8 | 0 | 16 | 0.00 | 0.0 | | |
| HSV HEK | −1 | 8/8 | 11 | 0 | 1.00 | 100.0 | 0.8 | 2.8 |
| MRH | −2 | 3/8 | 3 | 5 | 0.38 | 37.5 | | |
| 50K | −3 | 0/8 | 0 | 13 | 0.00 | 0.0 | | |
| HSV HEK | −2 | 8/8 | 13 | 0 | 1.00 | 100.0 | | |
| MRH | −3 | 3/8 | 5 | 5 | 0.50 | 50.00 | 0.0 | 4.0 |
| 5K | −4 | 2/8 | 2 | 11 | 0.15 | 15.4 | | |
| | −5 | 0/8 | 0 | 19 | 0.00 | 0.0 | | |
| HSV HEK | −2 | 8/8 | 13 | 0 | 1.00 | 100.0 | | |
| MRH | −3 | 4/8 | 5 | 5 | 0.50 | 50.0 | 0.0 | 4.0 |
| 5K + Gly | −4 | 1/8 | 1 | 12 | 0.08 | 7.7 | | |
| | −5 | 0/8 | 0 | 20 | 0.00 | 0.0 | | |

Example 2

Materials and Methods

Rabbits were immunized with either KLH conjugated Skeletal Tropin C (TropC; N=3) or LH conjugated TropC (N=3) Rabbit sera was collected at day 0 prior to immunization (pre-bleed), and at various points following immunization according to the following schedule.

| Pre-bleed | Day 0 |
| Primary immunization | Day 0 |
| Boost 1 | Day 21 |
| Test Bleed | Day 30 |
| Boost 2 | Day 42 |
| Production Bleed | Day 50 |
| Boost 3 | Day 71 |
| Production Bleed | Day 85 |

Continue Boost/Bleed cycle every 28 days through day 168

The antibody response to the immunizations was measured by ELISA to determine the following:

1) The presence of anti-LH antibodies in naïve rabbits;
2) Compare the immunogenicity of the carrier molecules (FIG. 1)
Screening antigen=purified KLH or LH
3) If there is cross-reactivity of antibodies generated against either carrier to the other (FIG. 3)
Screening antigen=purified KLH or LH
4) Assess the functionality of LH as a carrier protein to elicit an antibody response against a conjugated antigen (TropC) (FIG. 4)
Screening antigen=TropC Results Sera from 6 naïve rabbits was screened for reactivity against the LH antigen via ELISA. Pre-existing antibodies against LH were undetectable.

The immunogenicity of the carrier molecule was determined by screening sera from TropC-KLH or TropC-LH immunized rabbits against KLH or LH respectively by ELISA. The antibody titer generated against LH was significantly less than that generated against KLH at every point assayed (*=p≥0.05; **=0.05>p≥0.01.) See, FIG. 1.

The cross-reactivity of anti-KLH and anti-LH antibodies was measured by ELISA. Cross-reactive LH antibodies to KLH were not detected until after the fourth injection (Day 85). Cross-reactive KLH antibodies to LH were not detected until after the fourth injection (Day 85).

Figure 2:
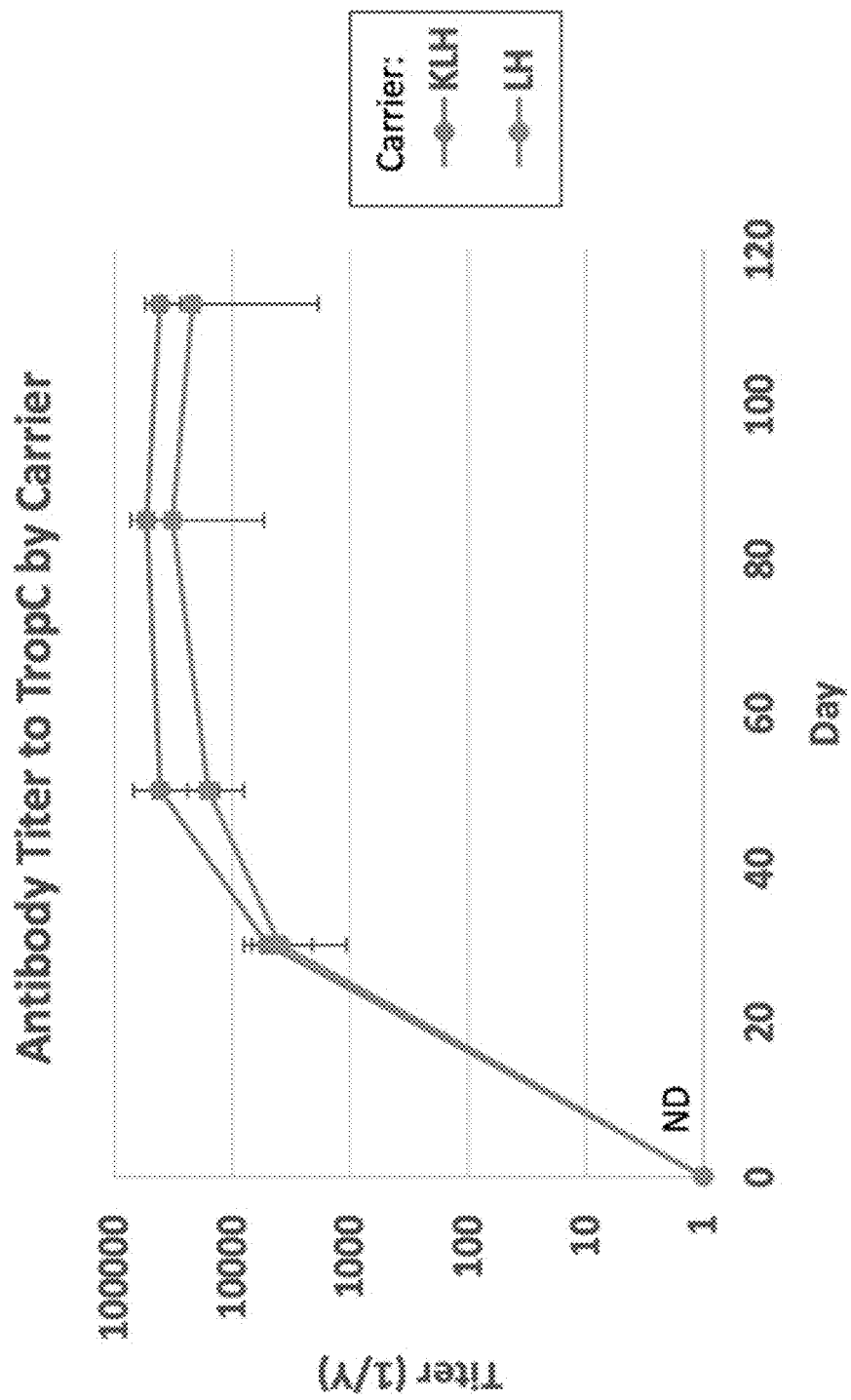
FIG. 2 is a graph showing that LH and KLH conjugated TropC generates a similar antibody response after 112 days.

Sera from rabbits immunized with TropC conjugated to either KLH or LH were tested for reactivity to TropC by ELISA. None of the titers were significantly different from each other (Students T test; P>0.05). Antibodies to TropC were not detected (ND) in the pre-immune sera. See, FIG. 2.

Conclusions

LH is an effective carrier protein and can be utilized to generate potent antibody responses. LH was as effective as KLH as an antigen carrier in this experiment, and has potential to be an alternative carrier to KLH. The low cross-reactivity of KLH antibodies to LH suggest that LH could be alternated in immunization protocols to reduce the immunodominance of the carrier molecule.

Although LH had reduced immunogenicity, the antibody response to it's conjugated antigen was not significantly different from KLH. After multiple immunizations the antibody response to a carrier molecule (particularly KLH) can dominate the immune response resulting in the reduction of antibody titer to its conjugated antigen. This is often the case with long immunization protocols, or when using poorly immunogenic antigens such as small peptides, steroids or haptens. Thus, the reduced immunogenicity of LH may make it a superior carrier to KLH when generating an antibody response to these antigens.

Example 3

Materials and Methods

Colon Adenocarcinoma Human Cells (Caco-2 ATTC HTB-37) were maintained in complete growth medium EMEM (Eagle's Minimum Essential Medium) in 6 well plate as $10^5$ cells/well for a 24-hour incubation under optimal conditions (37° C., 5% $CO_2$, and humidified atmosphere). One mL of each Hemocyanin (G and H) was added to each well and 6-well plate was incubated for 24 hours under optimal conditions and filtered using 0.45 μm sterile filters. Hemocyanin G is lobster hemocyanin glycosylated with honey 1% and Hemocyanin H is lobster hemocyanin alone.

Results

The results of this study demonstrated that, as compared to the control (Caco-2 cells and EMEM), Hemocyanin G had a substantially greater cytotoxic effect than Hemocyanin H.

It is understood that the examples and embodiments described herein are for illustrative purposes only and that various modifications or changes in light thereof will be suggested to persons skilled in the art and are to be included within the spirit and purview of this application and the scope of the appended claims.

All publications mentioned in this specification above or listed below are herein incorporated by reference as though fully set forth. Any discussion of documents, acts, materials, devices, articles or the like that has been included in this specification is solely for the purpose of providing a context for the present invention. It is not to be taken as an admission that any or all of these matters form part of the prior art base or were common general knowledge in the field relevant to the present invention as it existed anywhere before the priority date of this application.

What is claimed is:

1. A method of treating a proliferative disorder in a mammal afflicted therewith, said method comprising internally administering an effective amount of lobster hemolymph, lobster hemocyanin, or a derivative of lobster hemocyanin.

2. The method of claim 1, wherein the method comprises internally administering lobster hemocyanin purified or partially purified from lobster hemolymph or a derivative of such lobster hemocyanin.

3. The method of claim 1, wherein the method comprises internally administering a derivative of lobster hemocyanin that is selected from fragmented lobster hemocyanin, an active fraction of lobster hemocyanin or of fragmented hemocyanin, or a glycosylated form of lobster hemocyanin, an active fraction of lobster hemocyanin, or of fragmented lobster hemocyanin.

4. The method of claim 3, wherein the derivative of lobster hemocyanin is a glycosylated form of lobster hemocyanin or of fragmented lobster hemocyanin.

5. The method of claim 4, wherein the derivative of lobster hemocyanin is a glycosylated form of lobster hemocyanin or of fragmented lobster hemocyanin prepared by admixing the hemocyanin or fragmented hemocyanin with an aqueous sugar solution.

6. The method of claim 5, wherein the aqueous sugar solution is diluted honey.

7. The method of claim 3, wherein the derivative of lobster hemocyanin is a glycosylated form of lobster hemocyanin.

8. The method of claim 1, wherein the hemocyanin preparation is proteolyzed lobster hemocyanins prepared by admixing and reacting a protease with lobster hemocyanins for a time and under conditions such that the hemocyanins are proteolyzed.

9. The method of claim 1, wherein the lobster is *Homarus americanus, Homarus gammarus,* or *Panulirus argus.*

10. The method of claim 1, wherein the hemocyanin or derivative thereof is administered in a pharmaceutical composition comprising one or more sugars.

11. The method of claim 10 wherein the composition comprises honey.

12. The method of claim 1, wherein the lobster hemocyanin or derivative thereof is administered orally, transdermally, transmucosolly, or parenterally.

13. The method of claim 12, wherein the lobster hemocyanin or derivative thereof is administered orally or parenterally.

14. The method of claim 1, wherein the proliferative disorder is a cancer selected from a group consisting of solid tumors, carcinomas, sarcomas, Kaposi's sarcoma, erythroblastoma, glioblastoma, meningioma, astrocytoma, melanoma and myoblastoma, and leukemia.

15. The method of claim 14, wherein the method comprises co-administering a cancer antigen.

16. The method of claim 15, wherein the antigen is admixed with the lobster hemocyanin.

17. The method of claim 16, wherein the antigen is conjugated to the lobster hemocyanin.

18. A method of stimulating an immune response to an antigen in a mammal, said method comprising co-administering to the mammal the antigen and an adjuvant selected from lobster hemocyanin, fragmented lobster hemocyanin, an active fraction of lobster hemocyanin or of fragmented hemocyanin, or a glycosylated form of lobster hemocyanin, an active fraction of lobster hemocyanin, or of fragmented lobster hemocyanin.

19. The method of claim 18 wherein the antigen is conjugated to the lobster hemocyanin.

20. A method of treating a viral infection in a mammal afflicted therewith, said method comprising internally administering an effective amount of a lobster hemolymph, lobster hemocyanin, or a derivative of lobster hemocyanin.

21. The method of claim 20, wherein the mammal is treated for a viral infection selected from the group consisting of ebola viruses, Herpes Simplex Virus 1 (HSV-1), HSV-2, Herpes Zoster (VZV), Equine Herpesvirus-1, Feline Herpesvirus-1, Epstein-Barr virus, Human Immune Deficiency virus, Cytomegalovirus, human papilloma virus, rhinovirus, and influenza virus.

22. The method of claim 21, wherein the viral infection is an HSV infection.

23. The method of claim 22, wherein the viral infection is an HSV-1 infection.

24. The method of claim 20, wherein the derivative of lobster hemocyanin is selected from fragmented lobster hemocyanin, an active fraction of lobster hemocyanin or of fragmented hemocyanin, or a glycosylated form of lobster hemocyanin or of fragmented lobster hemocyanin.

25. The method of claim 24, wherein the hemocyanin preparation is proteolyzed lobster hemocyanins prepared by admixing and reacting a protease with lobster hemocyanins for a time and under conditions such that the hemocyanins are proteolyzed.

26. The method of claim 20, wherein the lobster hemocyanin or derivative thereof is administered orally, transdermally, transmucosolly, or parenterally.

27. The method of claim 20, wherein the lobster hemocyanin or derivative thereof is administered orally or parenterally.

28. The method of claim 20, wherein the lobster is *Homarus americanus, Homarus gammarus,* or *Panulirus argus.*

29. The method of claim 20, wherein the hemocyanin or derivative thereof is administered in a pharmaceutical composition comprising one or more sugars.

30. The method of claim 29, wherein the composition comprises honey.

* * * * *